United States Patent
Hess

(10) Patent No.: US 7,066,067 B2
(45) Date of Patent: Jun. 27, 2006

(54) MICROTOME

(75) Inventor: Hans-Juergen Hess, Leimen (DE)

(73) Assignee: Hess Consult GmbH, Leimen (DE)

( * ) Notice: Subject to any disclaimer, the term of this patent is extended or adjusted under 35 U.S.C. 154(b) by 127 days.

(21) Appl. No.: 10/470,222

(22) PCT Filed: Jan. 19, 2002

(86) PCT No.: PCT/DE02/00157

§ 371 (c)(1),
(2), (4) Date: Dec. 5, 2003

(87) PCT Pub. No.: WO02/061393

PCT Pub. Date: Aug. 8, 2002

(65) Prior Publication Data

US 2004/0099119 A1 May 27, 2004

(30) Foreign Application Priority Data

Feb. 1, 2001 (DE) ................................ 101 04 432

(51) Int. Cl.
*G01N 1/06* (2006.01)
*B26D 7/26* (2006.01)
(52) U.S. Cl. ..................... 83/167; 83/707; 83/915.5
(58) Field of Classification Search ............... 83/915.5, 83/15, 16, 167–171, 425, 435.11, 437.1, 703, 83/707, 713, 730
See application file for complete search history.

(56) References Cited

U.S. PATENT DOCUMENTS

| 2,961,908 | A | * | 11/1960 | Fernandez-Moran | ......... 83/170 |
| 3,103,844 | A | * | 9/1963 | Persson | ......... 83/167 |
| 3,377,898 | A | * | 4/1968 | Persson | ......... 83/78 |
| 3,699,830 | A | * | 10/1972 | Pickett | ......... 83/13 |
| 4,207,790 | A | * | 6/1980 | Endo | ......... 83/699.11 |
| 5,065,657 | A | * | 11/1991 | Pfeifer | ......... 83/703 |
| 5,551,326 | A | * | 9/1996 | Goodman | ......... 83/167 |
| 5,669,278 | A | * | 9/1997 | Metzner | ......... 83/915.5 X |
| 6,598,507 | B1 | * | 7/2003 | Gunther et al. | ......... 83/76.9 |

FOREIGN PATENT DOCUMENTS

| DE | 38 30 725 | 3/1990 |
| DE | 42 05 257 | 6/1993 |
| DE | 42 05 258 | 6/1993 |

* cited by examiner

*Primary Examiner*—Clark F. Dexter
(74) *Attorney, Agent, or Firm*—Bachman & LaPointe, P.C.

(57) ABSTRACT

A microtome, in particular a rotational microtome, comprising a base frame (10) on which is provided a specimen holding device (32) for performing a vertical cutting movement. The microtome further has a knife holding device (12) for a cutting element (24) which is formed by a cutting knife (26) or a cutting blade combined with a blade holder. A considerable cost saving and a substantially enhanced level of torsional stiffness and stability when the cutting forces take effect is achieved in that in the microtome the knife holding device (12) has two side plate portions (14) which project forwardly from the lower end portion (16) of the base frame (10).

8 Claims, 4 Drawing Sheets

MICROTOME

BACKGROUND OF THE INVENTION

The invention concerns a microtome comprising a base frame on which is provided a specimen holding device for performing a vertical cutting movement, and a knife holding device for a cutting element which is formed by a cutting knife or a cutting blade combined with a blade holder.

Such a microtome can be a table microtome or a cryostat microtome.

DE 42 05 257 C2 describes a rotational microtome comprising a base plate on which a base frame with a microtome housing is arranged at the rear and on which a knife holding device is arranged at the front. To receive thin sections of a thin section specimen which is clamped in the specimen holding device of the rotational microtome, that known rotational microtome has a trough configuration comprising two mutually spaced side portions and a front portion connecting the side portions together. The trough configuration therefore has a U-shaped area in plan, which matchingly encloses the knife holding device on three sides. The two side portions of the trough of U-shaped configuration terminate at least approximately flush with the rearward microtome housing at the outside thereof.

A microtome with a control desk which includes operating elements for setting various parameters such as section thickness feed speed, trimming section thickness, section thickness and optionally a display device for displaying the set parameters is known from DE 42 05 258 C2. That known microtome has a receiving portion which is adapted for releasably fixing the control desk. That known microtome also provides that the base frame with the microtome housing is arranged at the rearward end portion of a base plate and the knife holding device is arranged at the front end portion of the base plate.

Known microtomes, in particular rotational microtomes, usually have a base plate, at the rearward end portion of which the base frame is arranged and at the forward end portion of which is arranged the knife holding device. Such a base plate and mounting of the base frame and the knife holding device on the base plate involve an assembly complication and expenditure which has an effect on the manufacturing costs of such a known microtome. The base plate and mounting of the base frame and the knife holding device on the base plate can also have an adverse influence on torsional stiffness and stability of the microtome when the cutting forces become operative.

DE 38 30 725 A1 discloses a microtome having a drive device which has a shaft with a hand wheel arranged thereon, the hand wheel having a handle. An electromagnet is arranged on the housing frame of the microtome, for arresting the drive device. The electromagnet is in operative relationship with a switching ring displaceable axially on the shaft. A control device connected to the electromagnet and to a sensor controls the electromagnet in dependence on a signal from the sensor. That known microtome has a base frame with a specimen holding device. A base plate projects forwardly from the base frame, at the underside. Projecting vertically upwardly from the front edge of the base plate are two lateral columns, between which a cutting knife is arranged.

DE 88 09 096 U1 discloses a microtome having a housing on which are arranged operating knobs connected to a transmission arrangement for manually setting the parameters which can be selected at the microtome such as section thickness, knife angle and so forth. That known microtome has coaxial operating knobs at both sides, which can be alternately recessed in the microtome housing.

The German journal 'Zeitschrift für wissenschaftliche Mikroskopie und mikroskopische Technik', 63 (1958), pages 484 through 494, discloses conventional microtome structures comprising a base plate, on which a base frame with a specimen holding device is mounted at the rear and on which a knife holding device is mounted at the front. The base plate is for example of an inverted U-shaped cross-sectional profile, on which a pattern carrier slide with a knife holder is in turn disposed so that the working and manipulation plane for the operator of the microtome is relatively high. That is disadvantageous from ergonomic points of view. A corresponding consideration also applies in regard to the microtome which is known from the prospectus from Leitz, Wetzlar: 'Serienschnittmikrotom', 1510 (1974), page 2, and which also has a box-shaped base element which projects away from the rear base frame with the specimen holding device, at the underside thereof, and on which the blade holding device which is in the form of a blade block is displaceably mounted. The base element involves a relatively great heightwise dimension, and that has a disadvantageous effect on ergonomy and operating comfort.

The object of the present invention is to provide a microtome of the kind set forth in the opening part of this specification, with which it is possible to achieve considerable cost savings, which involves a substantially enhanced level of torsional stiffness and stability when the cutting forces become operative.

SUMMARY OF THE INVENTION

In accordance with the invention, in a microtome of the kind set forth in the opening part of this specification, that object is attained in that the knife holding device has two side plate portions which project forwardly from the lower end portion of the base frame. In this case the two side plate portions of the knife holding device can be screwed or welded to the base frame. It is preferable however if the two side plate portions of the knife holding device are formed integrally with the base frame, that is to say are cast in one piece therewith.

The microtome according to the invention, in particular a rotational microtome, therefore eliminates a specific base plate. The function of such a base plate in known microtomes is embodied, in the microtome according to the invention, by the modified base frame, that is to say which is connected directly to the knife holding device. Besides a considerable reduction in cost, that design configuration affords the quite considerable advantage of substantially increased torsional stiffness and stability when the cutting forces come into action, that is to say during the cutting operation.

The two side plate portions which project forwardly from the lower end portion of the base frame can be provided for directly and immediately receiving and holding the cutting element, but the two side plate portions may also each have an adjustable support for receiving and holding the cutting element.

The design configuration of the microtome according to the invention, with two side plate portions which project forwardly from the lower end portion of the base frame, affords between the side plate portions in front of and behind the cutting element, that is to say the cutting knife or the cutting blade combined with a blade holder, a free space which is of optimum suitability for catching the cutting waste pieces or for catching thin sections. A catch trough can be provided for that purpose between the two side plate portions.

While, in known microtomes, in particular rotational microtomes, thin sections which are not required or trimming material which is not required are usually brushed at the center of the unit upwardly over the cutting element behind the knife holding device and drop on to the base plate so that, for example when processing a relatively large number of paraffin specimen blocks, a considerable, troublesome cutting waste builds up between the knife holding device and the front side of the microtome housing which contains the base frame, the microtome according to the invention, of the last-mentioned design configuration, has the advantage that cutting waste pieces drop in specifically targeted relationship into the above-mentioned catch trough. If necessary additional cutting waste troughs can be disposed laterally outside the two side plate portions.

It may be desirable in regard to the microtome according to the invention if the catch trough is combined with a section stretching trough which extends with a trough portion between the two side plate portions. While the catch trough is what is known as a dry trough, the section stretching trough is desirably filled with a suitable liquid, for example with warm water, in order to implement stretching of the thin sections. In the case of a microtome of the last-mentioned kind the catch trough is disposed behind the knife holding device, that is to say behind the cutting element in the region between same and the microtome housing and—as has been stated above—serves as a dry cutting waste trough. The section stretching trough can be for example in the form of a heatable water bath, it is disposed directly under or in front of the knife holding device, that is to say on the front side of the knife holding device, the front side being remote from the microtome housing. The catch trough and the section stretching trough can be independent troughs which are separate from each other. It is also possible for the catch trough and the section stretching trough to be integrally connected together.

In the case of a microtome of the last-mentioned kind, the thin sections which are wanted or required can be advantageously passed over a very short distance by means for example of a brush directly downwardly to the section stretching trough in order to provide for stretching of the thin sections. Consequently the microtome according to the invention makes it possible to implement ergonomic work with an increased level of safety and operating comfort because lateral twisting of the upper body when transferring a section into a section stretching bath which is disposed laterally beside the microtome to the right or the left thereof, such twisting movement being required in known microtomes and especially rotational microtomes and being harmful to health, is now eliminated. Hitherto, the known microtome design configurations prohibited the section stretching bath from being positioned in front of the base plate of the microtome also for the reason that the increase in lengthwise dimension resulting therefrom made it virtually impossible to operate the microtome. That applies in particular in regard to rotational microtomes which are to be operated manually.

All those deficiencies of known microtomes, in particular rotational microtomes, are eliminated in a very simple manner in the microtome according to the invention.

BRIEF DESCRIPTION OF THE DRAWINGS

Further details, features and advantages will be apparent from the description hereinafter of embodiments of the microtome according to the invention and essential parts thereof, as diagrammatically illustrated in the drawing in which.

DETAILED DESCRIPTION

Figure 1:
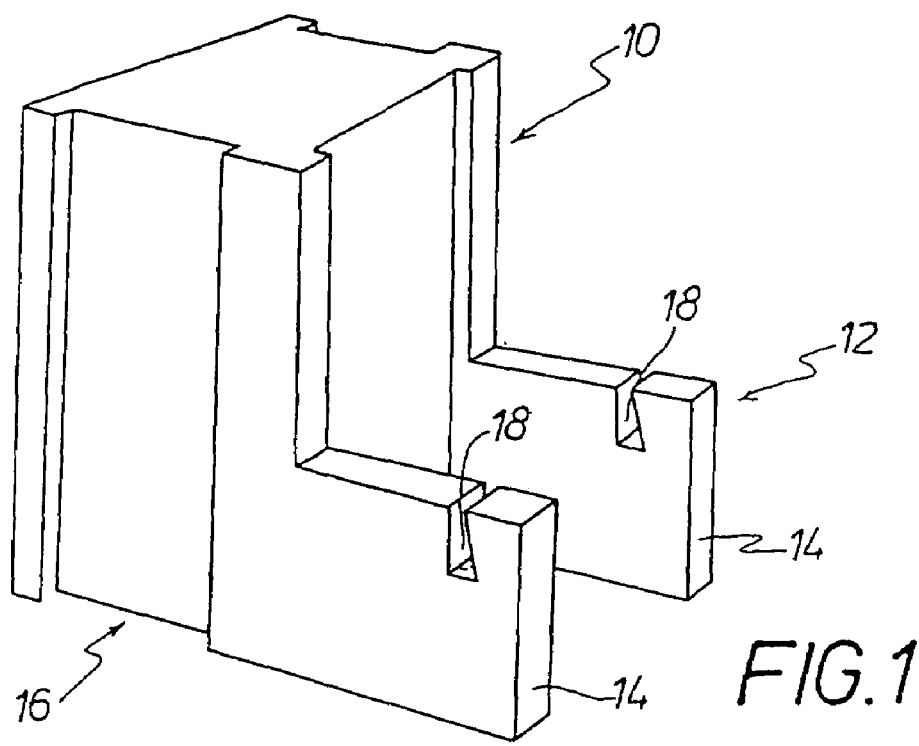
FIG. 1 is a perspective view of a first configuration of the base frame of the microtome.

FIG. 1 is a perspective view showing a base frame 10 of a microtome, in particular a rotational microtome, from which a knife holding device 12 integrally projects. The knife holding device 12 is formed by two side plate portions 14 which project forwardly from the lower end portion 16 of the base frame 10. The two side plate portions 14 are each provided with a respective recess 18 which are provided for receiving a cutting element (not shown). That cutting element may involve a cutting knife or a cutting blade combined with a blade holder.

Figure 2:
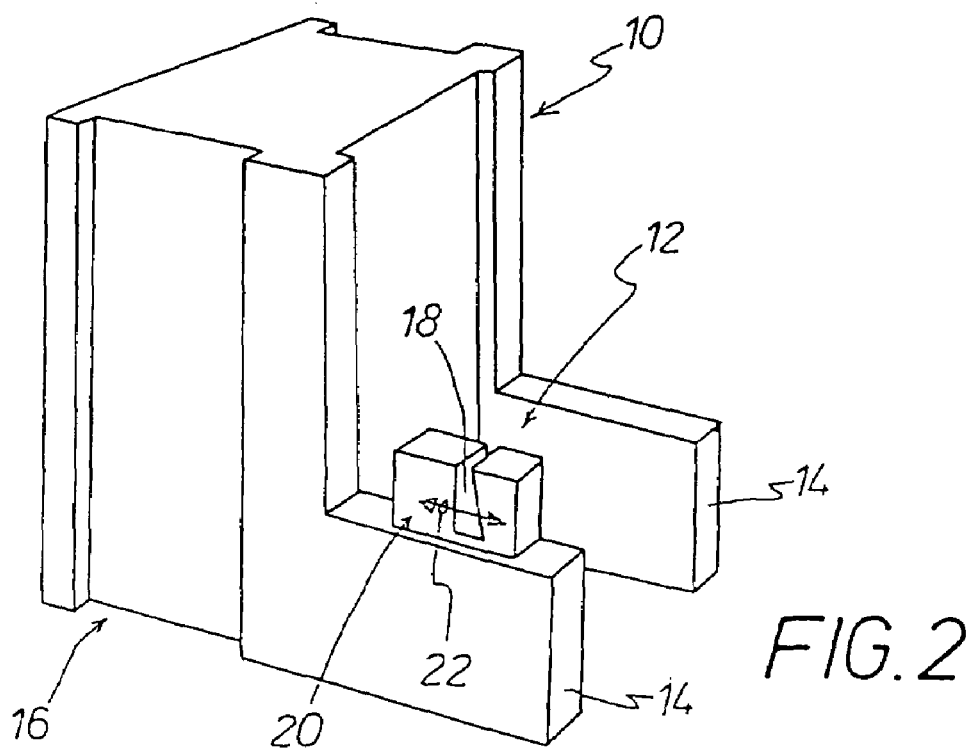
FIG. 2 is a perspective view similar to FIG. 1 for diagrammatically illustrating a second configuration of the base frame of the microtome.

While FIG. 1 shows a configuration in which the recesses 18 are provided directly and immediately in the side plate portions 14, FIG. 2 diagrammatically shows a configuration of a base frame 10 in which the recesses 18 are each provided in a respective support 20 of which only one of the two supports 20 is illustrated in FIG. 2. The supports 20 are arranged to be simultaneously linearly movably guided on the side plate portions 14. The linear mobility of the supports 20 is indicated by the double-headed arrow 22.

The embodiment shown in FIG. 2 also provides that the two side plate portions 14 project forwardly from the lower end portion 16 of the base frame 10 of the microtome, in particular a rotational microtome. In this embodiment also the two supports 20 with their recesses 18 form the knife holding device 12, wherein the cutting element (also not shown in FIG. 2) can be adjusted as desired in relation to the base frame 10 and thus in relation to a specimen holding device 32.

Figure 3:
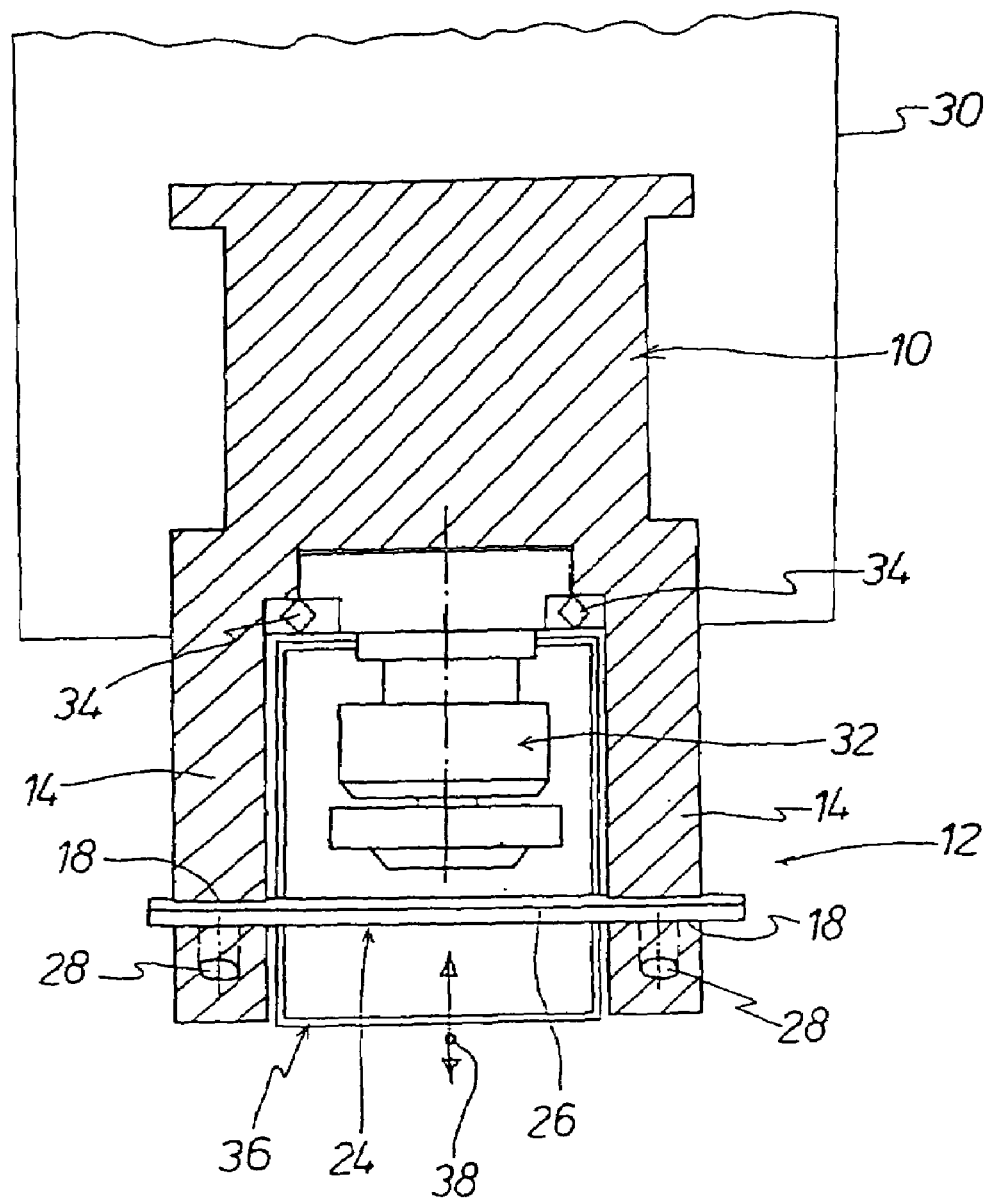
FIG. 3 is a diagrammatic plan view in section of the microtome with a catch trough, that is to say a dry trough.

FIG. 3 is a view in section showing the base frame 10 with the side plate portions 14 which project forwardly away from the base frame 10 and which are each provided with a respective recess 18 for forming a knife holding device 12 for a cutting element 24. The cutting element 24 is formed by a cutting knife 26 which is clamped fast between the two side plate portions 14. This is indicated by the two screwthreaded holes 28 into which screw members (not shown) are screwed.

The specimen holding device 32 is guided linearly movably vertically up and down on linear guide elements 34 on the base frame 10 which is arranged in a microtome housing 30 of which a portion is diagrammatically indicated here. A thin section specimen can be clamped in the specimen holding device 32.

A catch trough 36 is or can be arranged between the two side plate portions 14 which project forwardly from the base frame 10. The catch trough 36 is provided beneath the cutting element 24 so that it can be withdrawn from and pushed again into the space between the two side plate portions 14. This is indicated by the double-headed arrow 38. The catch trough 36 consequently has no effect on the depth dimension of the microtome so that the microtome for example can be designed without any problem in the form of a rotational microtome which is to be actuated manually, with a drive hand wheel which projects laterally from the outer microtome housing 30.

Figure 4:
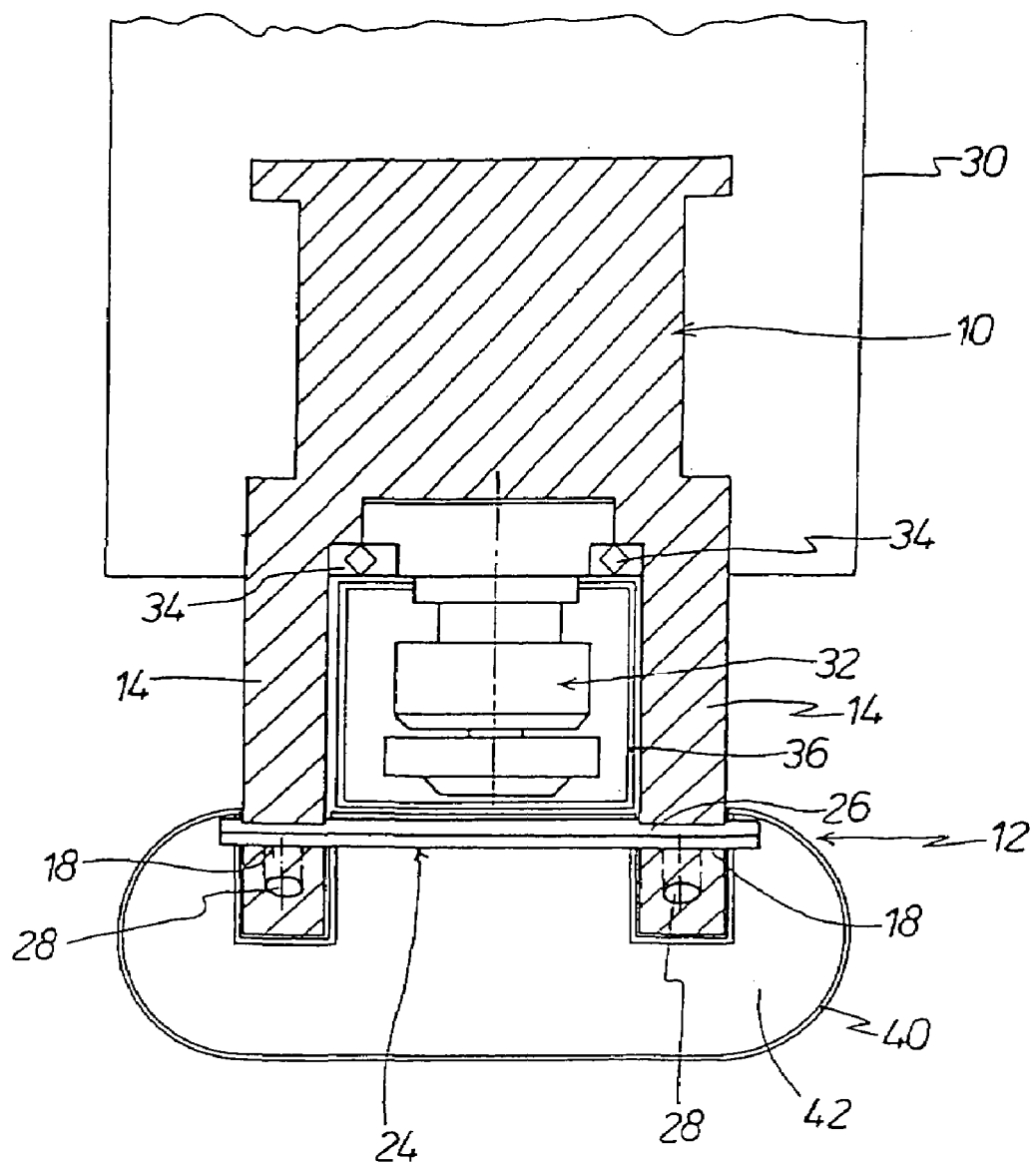
FIG. 4 is a view similar to FIG. 3 of a configuration of the microtome in which a catch or dry trough is combined with a section stretching trough filled with a suitable liquid.

FIG. 4 is a view similar to FIG. 3 diagrammatically showing a configuration in which the dry catch trough 36 is combined with a section stretching trough 40. In this case the catch trough 36 can be connected to the section stretching trough 40, while another possibility provides that the catch trough 36 and the section stretching trough 40 are mutually separated units. The section stretching trough 40 is filled with a suitable liquid, for example with warm water 42. For that purpose the section stretching trough 40 can be provided with a heating device. While the catch trough 36 is provided as a dry trough behind the cutting knife 26, the section stretching trough 40 is disposed below and in front of the cutting knife 26, and it extends for example around the side plate portions 14 at the front laterally as far as the cutting knife 26.

The same features are denoted in FIG. 4 by the same references as in FIG. 3 so that there is no need for all those features to be described in detail once again with reference to FIG. 4.

Figure 5:
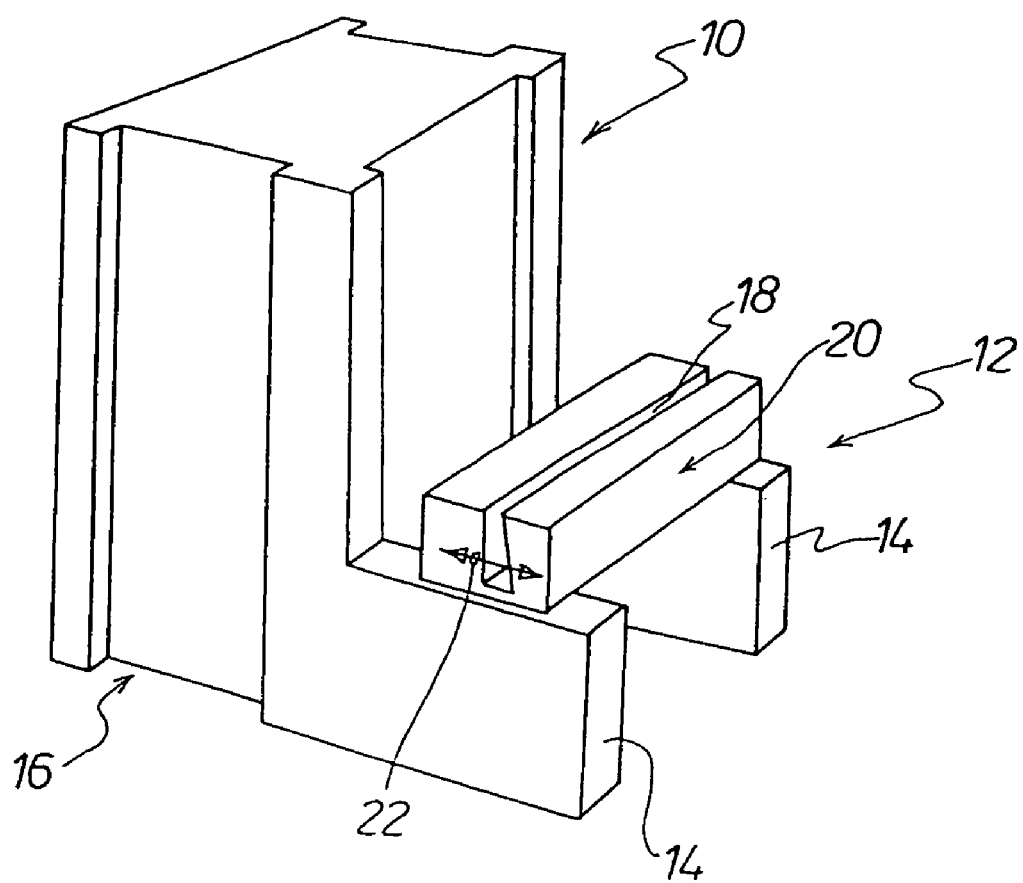
FIG. 5 is a perspective diagrammatic view similar to FIGS. 1 and 2 of a third embodiment of the base frame of the microtome.

FIG. 5 is a perspective view similar to FIGS. 1 and 2 showing a base frame 10 of a microtome, in particular a rotational microtome. A knife holding device 12 projects integrally away from the base frame 10. The knife holding device 12 is formed by two side plate portions 14 which project forwardly away from the lower end portion 16 of the base frame 10. Arranged on the two side plate portions 14 is a displaceable support 20 which bridges across the two side plate portions 14. The support 20 is linearly movably guided on the side plate portions 14. That is indicated by the double-headed arrow 22.

The support 20 which bridges across the two side plate portions 14 is provided with a recess 18 which serves to receive a cutting knife or cutting element (not shown).

The invention claimed is:

1. A microtome comprising:
    a base frame (10) on which is provided a specimen holding device (32) for performing a vertical cutting movement, and
    a knife holding device (12) for a cutting element (24) which is formed by a cutting knife (26) or a cutting blade combined with a blade holder, wherein the knife holding device (12) has two discrete side plate portions (14) which are of identical configuration, which are fixed to the base frame (10), and which project forwardly from the lower end portion (16) of the base frame (10), each in a cantilever configuration, and prolong the base surface of the base frame (10) forwardly so that the two side plate portions (14) form for the base frame (10) an increase in the support surface on which the base frame stands, the microtome further comprising between the two side plate portions (14) means for receiving waste cuttings.

2. A microtome as set forth in claim 1, wherein the side plate portions (14) of the knife holding device (12) are screwed or welded to the base frame (10).

3. A microtome as set forth in claim 1, wherein the side plate portions (14) of the knife holding device (12) are formed integrally with the base frame (10).

4. A microtome as set forth in one of claims 1 through 3, wherein the two side plate portions (14) are provided for directly and immediately receiving and holding the cutting element (24).

5. A microtome as set forth in one of claims 1 through 3, wherein the two side plate portions (14) each have a respective displaceable support (20) for receiving and holding the cutting element (24).

6. A microtome as set forth in one of claims 1 through 3, wherein a displaceable support (20) for receiving and holding a cutting element (24) is provided on the two side plate portions (14), the support (20) bridging across the two side plate portions (14).

7. A microtome as set forth in claim 1, wherein the means for receiving waste cuttings comprises a catch trough (36) provided between the two side plate portions (14).

8. A microtome as set forth in claim 7, wherein the catch trough (36) is combined with a section stretching trough (40) which extends with a trough portion between the two side plate portions (14).

* * * * *